United States Patent [19]

Templeton et al.

[11] Patent Number: 5,325,227
[45] Date of Patent: Jun. 28, 1994

[54] LASER ATTENUATION MEANS

[75] Inventors: Douglas W. Templeton, Macomb County, Mich.; C. H. Chen, Knox County; W. R. Garrett, Anderson County, both of Tenn.; M. G. Payne, Bulloch County, Ga.

[73] Assignee: The United States of America as represented by the Secretary of the Army, Washington, D.C.

[21] Appl. No.: 111,322

[22] Filed: Aug. 23, 1993

[51] Int. Cl.⁵ ................................................ G02B 5/23
[52] U.S. Cl. .................................... 359/241; 359/297; 359/614; 372/11
[58] Field of Search ............... 359/241, 297, 601, 614; 372/29, 101, 11, 9

[56] References Cited

U.S. PATENT DOCUMENTS

| | | | |
|---|---|---|---|
| 3,734,592 | 5/1973 | Sztankay et al. | 359/736 |
| 3,775,586 | 11/1973 | Flint et al. | 219/121 L |
| 4,719,342 | 1/1988 | Cohn et al. | 359/297 |
| 4,846,561 | 7/1989 | Soileau, Jr. et al. | 350/354 |
| 4,917,481 | 4/1990 | Koechner | 359/297 |
| 5,080,469 | 1/1992 | McCahon et al. | 359/241 |
| 5,081,542 | 1/1992 | Efron et al. | 359/41 |
| 5,102,213 | 4/1992 | Lee et al. | 359/890 |

Primary Examiner—Rodney B. Bovernick
Assistant Examiner—Hemang Sanghavi
Attorney, Agent, or Firm—Peter A. Taucher; Gail S. Soderling

[57] ABSTRACT

The present invention provides protection from lasers with a high nonlinear absorption structure including a mirror which directs an incident beam to a beam splitter. A focusing lens receives and focuses the radiation to a higher intensity beam which is directed into an absorption material with a third order polarization property. Such materials will cause a two-photon absorption partial attenuation from the intensified beam when the incident radiation intensity is greater than ambient intensity. A focusing mirror receives the partially attenuated beam and reflects and refocuses the partially attenuated beam back through the absorption material, which now acts as a single photon absorption material to further attenuate the beam. The doubly attenuated beam passes through the focusing lens which recollimates the doubly attenuated beam and directs it to the beam splitter which in turn directs the beam to the receiving device. A normal intensity beam will not activate the absorption mechanism of the absorption material and will pass through the system essentially unaffected.

7 Claims, 1 Drawing Sheet

LASER ATTENUATION MEANS

GOVERNMENT INTEREST

The invention described herein may be manufactured, used and licensed by or for the Government for governmental purposes without payment to me of any royalty.

BACKGROUND OF THE INVENTION

1. Field of the Invention

In one aspect this invention relates to eye protection for combat personnel. In yet a further aspect, this invention relates to methods of absorbing light beams.

2. Prior Art

Laser technology has become an increasingly important part of modern technological warfare. Lasers are used in aiming devices, range finders, and as countermeasures to defeat various optical aiming and ranging devices.

As part of the development of laser technology, tuneable dye lasers are being developed which are obtained by pumping from other lasers or flash lamps. Such lasers provide high energy pulses and can be made in large variety of different wave lengths. The Ti-Sapphire lasers now being developed can also provide high repetitions of tuneable energy. This means the exact wave length used by an opponent can not be known in advance requiring that any acceptable absorption device be useful over a broad spectrum.

Thus, battlefield personnel are in danger of being exposed to laser radiation either casually or intentionally. With the power densities available from today's technology, serious damage will be done to unprotected eyes and also the optical devices used on combat vehicles. The radiation comes in discrete bursts of energy ranging from a few microjoules up to several joules in intensity and for periods of time from a few nanoseconds to a few microseconds.

To prevent eye damage, any light absorption device must react quickly, on the order of less than 10 picoseconds and absorb light in the range of 400 to 700 nm. Because of the limited time to react, the device must operate passively. A further constraint is the device must transmit light of normal intensity so the user can function in normal light conditions while bursts of high intensity are absorbed. This implies that the absorption material operates in nonlinear manner.

Attempts have been made to develop goggles which are suitable for attenuating the incoming laser beams during the last several years. The attenuation must be to a power level of less than 10 $\mu j$ which represents an attenuation factor of at least 10,000 since the available lasers can deliver up to several joules of power in the beam with little beam divergence. Partial solutions for beams at a preselected wave length have been achieved; however, there presently exists no protective goggles for personnel which are passive, can absorb a broad spectrum of high intensity beams, and simultaneously allow the user to function under normal light conditions.

BRIEF SUMMARY OF THE INVENTION

The problems of the prior art personnel goggles and device protector shields are overcome by the present invention which provides protection with a high nonlinear absorption coefficient. Devices made according to this invention provide a high attenuation while still allowing normal functioning.

A device according to this invention will have a reflecting mirror adapted to receive and direct the incident radiation onto the incident surface of a beam splitter which transmits a substantial portion of the incident radiation. A focusing lens placed on the side of the beam splitter opposite the reflecting mirror receives and focuses the radiation to a narrowly defined focusing area which further intensifies the radiation beam.

An absorption material is located at the focusing area the absorption material adapted to receive the focused radiation within its volume. The absorption material has a third order polarization property which allows it to act as a two-photon absorption media with respect to the intensified light beam coming from the focusing lens at frequencies where the radiation intensity is greater than normal ambient light intensity. The absorption material partially attenuates the focused beam as it passes through the absorption material by virtue of two-photon absorption.

After the focused beam has passed through the absorption material, there is a decay constant which allows the material to function as a single-photon absorption material after the decay time has elapsed to allow further photon absorption and further beam attenuation.

A focusing means, such as a focusing mirror is located on the side of the absorption material opposite the focusing lens, the focusing means receives the partially attenuated beam then reflects and refocuses the partially attenuated beam back through the absorption material, which now acts as a single photon absorption material in the focusing area. The beam is further attenuated by single photon absorption. The now doubly attenuated beam passes through the focusing lens which recollimates the doubly attenuated beam and transmits it to the second surface of the beam splitter. The beam splitter direct the beam to the receiving device.

A normal intensity beam will not have sufficient power to activate the absorption mechanism in the absorption material and will pass through the system essentially unaffected.

DETAILED DESCRIPTION OF PREFERRED EMBODIMENTS

Figure 1:
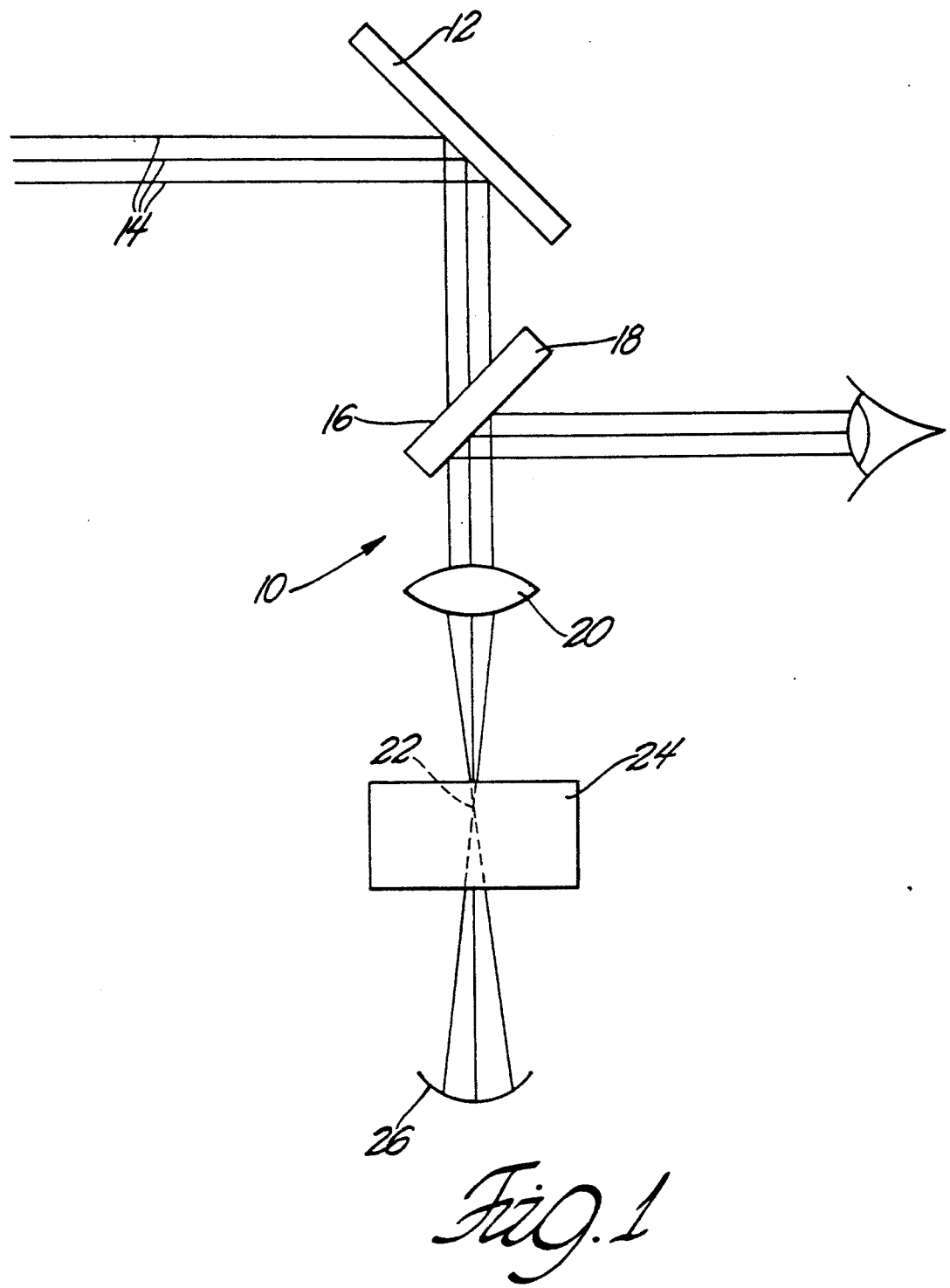
FIG. 1 is a schematic of a device made according to this invention.

Referring to the accompanying drawing, one device constructed in accordance with this invention 10 has a reflecting mirror 12 which is designed to receive an incoming beam 14. The incoming beam 14 is reflected by the mirror 12 and directed as a columnar beam onto an incident surface 16 of a beam splitter 18.

The beam splitter 18 is designed to transmit a substantial portion. The typical beam splitter used in this work is 50% transmission and 50% reflection. Such structures are well known in the art. One example of a suitable structure is, Newport Broadband 50/50 Dielectric Beamsplitter (Model 60Q10).

A focusing lens 20 is placed on the side of beam splitter 18 opposite the reflecting mirror 12 where it can receive and focus the radiation beam 14 after it passes through the beam splitter. This results in a narrowly defined focusing area 22, with a further intensified radiation beam. The focusing lens is used to intensify the radiation because the photon absorption phenomena is intensity dependant with a more intense beam having a higher photon absorption.

A block of absorption material 24 is located at the focusing area 22 the absorption material receiving the focused beam of radiation within its structure. The absorption material will be chosen from the class of materials which have a high third order susceptibility coefficient and which are transparent. Materials with high third order susceptibility coefficients can attenuate an intense beam of radiation by a two photon absorption mechanism. The value of the third order susceptibility coefficient can be determined by measuring two-photon absorption coefficient $\beta$. The attenuation of an incident beam is a function of $\beta$ which is proportional to the two photon absorption of the material. Attenuation of an incident beam is a function of $\beta$ and the original intensity. A material with a $\beta$ on the order of $10^{-8}$ cm/Watt would attenuate the incident beams by $10^4$ only when the incident beam is on the order of $10^{12}$ Watts/cm$^2$, which is much higher than most lasers expected to be used in the battle field. The $\beta$ for most known transparent absorptive materials has a range of $10^{-9}$ to $10^{-10}$ cm/Watt. These materials will slightly attenuate an incident beam by two photon absorption; however, this is not sufficient attenuation power to fully protect the eyes of a person exposed to the radiation.

It is desirable the material thickness be as thin as possible. However, the thickness of the absorptive material must be large when compared to the confocal parameter of the lens so the absorption takes place within a few confocal parameters of either side of the focal point.

When the beam passes through the absorption material, the absorption of photons raises the energy state of the materials components at a molecular level after which there is a decay from the energized state leaving a material which functions as a single photon absorption material having an attenuation factor higher than $10^4$ after the decay time. This single photon absorption material has sufficient additional attenuation potential to reduce the beam strength to a safe level for the human eye and sensitive optical devices.

A focusing mirror 26 is located on the side of the absorption material 24 opposite the focusing lens 20, the focusing mirror reflecting and refocusing the partially attenuated beam back through the absorption material. The distance between the absorption material is sufficient that the travel time to the focusing mirror 26 and back will allow the absorption material 24 to decay to the single photon absorption state. This distance need be only a fraction of a centimeter which allows the device of this invention to be made compact enough to be placed in hand held optical devices such as optical range finders.

The refocused beam passes through the absorption material at the focusing area with the material now acting as a single photon absorber to further attenuate the beam by single photon absorption. The now doubly attenuated beam passes through the focusing lens 20 which recollimates the beam, and the collimated beam from the focusing lens reflecting off second surface of the beam splitter 18 to the receiving device shown as a human eye.

Examples of suitable absorptive materials are the phthalocyanine polymeric materials. Such materials have double bonds and a variety of possible states for the electrons associated with the molecular structure so photons of various wave lengths can be absorbed. Also, once two photons have been absorbed the material will rapidly quench to a state where it is a strong single photon absorber. It has also been discovered that buckminster fullerene having about 60 atoms or more when dissolved in toluene will provide an acceptable absorption material.

EXAMPLE

To test the proposed construction, an experimental device corresponding in construction to the FIG. was constructed. A Quanta Ray DC Nd:YAG multimode Q-switched laser with a beam divergence of 0.5 milliradian was used for a beam source. The laser can deliver pulse length of 7 nanoseconds and the frequency was doubled to produce 532 nm light. The Q-switch was activated once every five seconds with the laser cavity oscillation at 10 Hz.

Power measurements were performed using a Coherent 210 power meter while the laser operated at 10 Hz. Power reflecting off mirrors was measured using Gentec ED-100A Joulemeter connected to a Tektronix oscilloscope.

The laser beam was focused onto a standard reflecting mirror which received the incoming beam. The incoming beam was reflected by the mirror and directed as a columnar beam on to the incident surface of a Newport Broadband beam splitter. The beam splitter transmitted a substantial portion of the incident radiation.

The beam transmitted entered a 10 cm focal length lens located about 10 cm from the beam splitter. The lens received and focused the beam in a narrowly defined focusing area. This focusing substantially intensified the beam so the absorption by two-photon absorption process can be substantial. The focusing lens is used to intensify the radiation because photon absorption phenomena is intensity dependant and nonlinear with a more intense beam having a higher photon absorption.

A solution of phthalocyanine polymeric material absorption material about 1 cm thick was located with its face about 9.5 cm away from the focusing lens at the focusing area; the absorption material encompassed the focusing area within its volume. It is desirable the material thickness be as thin as possible and in practice the material thickness will be as thin as needed to provide the necessary thickness to surround the expected focusing zone which is a few confocal parameters on either side of the focal point.

The attenuated beam passed through the absorption material and onto a 5 cm focal length spherical mirror located about 4.8 cm from the face of the absorption material. The focusing mirror reflected and refocused the partially attenuated beam back through the absorption material. The distance between the absorption material was sufficient to allow the absorption material to decay to the single photon absorption state.

The refocused beam passed through the absorption material at the focusing area with the material now acting as a single photon absorber to further attenuate the beam by single photon absorption. The now doubly attenuated beam passed through the focusing lens again which recollimated the beam and directed the collimated beam onto the back surface of the beam splitter. The beam splitter reflected the beam onto a sensor.

The measured energy at the sensor was 2 microjoules or less which is below the threshold of permanent eye damage.

Various modifications and alterations will become apparent to those skilled in the art without departing from the scope and spirit of this invention and it is understood that this invention is not limited to the illustrative embodiments set forth above.

What is claimed is:

1. An eye protection device adapted to protect against a broad spectrum of incident high intensity radiation while allowing the transmission of normal radiation levels, including: a reflecting mirror adapted to receive and direct the incident radiation onto the incident surface of a beam splitter which transmits a substantial portion of the incident radiation; a focusing lens placed on the side of the beam splitter opposite the reflecting mirror, the lens receiving and focusing the radiation to a narrowly defined focusing area to further intensify the radiation beam; an absorption material located near the focusing area the absorption material adapted to receive the focused radiation, the absorption material having a third order susceptibility property which allows the material to act as a two photon absorption media with respect to the intensified light beam at frequencies where the radiation intensity is greater than normal ambient light intensity, the material having a decay constant which allows the material to function as a single photon absorption material after the decay time and after the beam has passed through the absorption material; and a focusing mirror located on the side of the absorption material opposite the focusing lens, the focusing mirror reflecting and refocusing the partially attenuated beam back through the absorption material at the focusing area to further attenuate the beam by single photon absorption the doubly attenuated beam passing through the focusing lens to collimate the beam, the collimated beam from the focusing lens reflecting from the second surface of the beam splitter to the receiving device.

2. The system of claim 1, where the absorption media is a phthalocyanine material dissolved in an organic solvent.

3. the system of claim 2, where the phthalocyanine material has a metal atom entrapped therein.

4. The system of claim 1, where the absorption media is a phthalocyanine material disposed as a thin film.

5. The system of claim 4, where the Buckminster fullerene has a metal atom entrapped therein.

6. The system of claim 1, where the absorption media is a Buckminster fullerene having at least 60 atoms suspended in a silica gel.

7. The system of claim 1, where the absorption media is a Buckminster fullerene dissolved in an organic solvent.

* * * * *